United States Patent [19]
Suzuki

[11] Patent Number: 5,628,796
[45] Date of Patent: May 13, 1997

[54] INTRAOCULAR LENS

[76] Inventor: Taketoshi Suzuki, 16, Kichikoji, Mizusawa-shi, Iwate-ken, Japan

[21] Appl. No.: 495,225

[22] Filed: Jun. 27, 1995

[30] Foreign Application Priority Data

Jul. 4, 1994 [JP] Japan .................. 6-174799

[51] Int. Cl.⁶ .................................. A61F 2/16
[52] U.S. Cl. ........................................... 623/6
[58] Field of Search ................................ 623/6

[56] References Cited

U.S. PATENT DOCUMENTS

| | | | |
|---|---|---|---|
| 4,240,163 | 12/1980 | Galin | 623/6 |
| 4,262,370 | 4/1981 | Hartstein | 623/6 |
| 4,404,694 | 9/1983 | Kelman | 623/6 |
| 4,575,374 | 3/1986 | Anis | 623/6 |
| 4,591,358 | 5/1986 | Kelman | 623/6 |
| 5,047,052 | 9/1991 | Dusroff | 623/6 |
| 5,071,432 | 12/1991 | Baileoff | 623/6 |

*Primary Examiner*—Mary Beth Jones
*Attorney, Agent, or Firm*—Flynn, Thiel, Boutell & Tanis, P.C.

[57] ABSTRACT

An intraocular lens (1) to be implanted in an anterior chamber (7) comprises a disk-shaped lens body (2) and a plurality of support legs (3, 4, 5, 6) extending in two opposite directions. The support legs (3, 4, 5, 6) are long enough for their distal ends (31, 41, 51, 61) to engagingly sit in ciliary sulci (9) when the support legs (3, 4, 5, 6) are inserted in and through fine bores or apertures 10 made by incision in a peripheral site of an iris (8).

2 Claims, 2 Drawing Sheets

INTRAOCULAR LENS

BACKGROUND OF THE INVENTION

1. Field of the Invention

This invention relates to an intraocular lens and more particularly to an intraocular lens to be implanted in the anterior chamber of an eye.

2. Description of the Related Art

Intraocular lenses have been used for years for implantation after surgery such as extracapsular cataract extraction, ultrasonic emulsifying aspiration, and so on. Most typical intraocular lenses are those to be implanted within lens capsules in posterior chambers (hereinafter called posterior chamber lenses). However, there are some particular conditions of surgery which make it impossible to fix the intraocular lens in the posterior chamber. In such cases, the intraocular lens, after being placed in the posterior chamber, must be sutured to the ciliary sulcus; otherwise, it is placed in the anterior chamber.

Suturing an intraocular lens to a ciliary sulcus is a very difficult technique which requires a high skill and expensive equipment for removal of a front part of the vitreous body. Moreover, since this method makes a large surgical invasion, it may cause any trouble in the oculus, or some other troubles which are currently unknown but may possibly be realized after many years.

In contrast, implantation of an intraocular lens in the anterior chamber requires neither a high skill nor expensive equipment. However, intraocular lens so far available for placement in the anterior chamber (hereinafter called anterior chamber lenses) were designed to be fixed by engagement with the anterior chamber angle. Therefore, these anterior chamber lenses were liable to damage a wide area of the anterior chamber angle. Moreover, internal support of conventional anterior chamber lenses was unreliable and could not prevent their rotating or other motional displacement. These could be large factors in inflammation or other like troubles of the corneal endothelium which might further invite damage to the iris after surgery.

OBJECT OF THE INVENTION

It is therefore an object of the present invention is to provide an intraocular lens to be implanted in an anterior chamber, easy to support therein, reliably fixed in place, and remarkably safe without damaging the tissues around it.

SUMMARY OF THE INVENTION

According to the invention, there is provided an intraocular lens comprising a lens body and elongated extensions extending from an outer circumferential margin of the lens body, the elongated extensions being long enough for their distal ends to engagingly sit in grooves of a ciliary body, i.e. ciliary sulci, when the elongated extensions are inserted into and beyond fine apertures made by incision in a peripheral site of an iris.

The intraocular lens according to the invention, when used, is fixed in an anterior chamber by placing the lens body in the anterior chamber and by simultaneously inserting the elongated extensions into fine apertures made by incision in the peripheral site of the iris. Then the distal ends of the elongated extensions go beyond the fine apertures and engagingly sit in in the ciliary sulci. As a result, the lens body is fixed stationarily in place in the anterior chamber. Fine apertures can be made so small that they do not disturb the movement of the iris.

The foregoing and other objects, features and advantages of the invention will become more apparent in the light of the following description of a preferred embodiment thereof, as illustrated in the accompanying drawings.

DETAILED DESCRIPTION OF THE PREFERRED EMBODIMENTS

Figure 1:
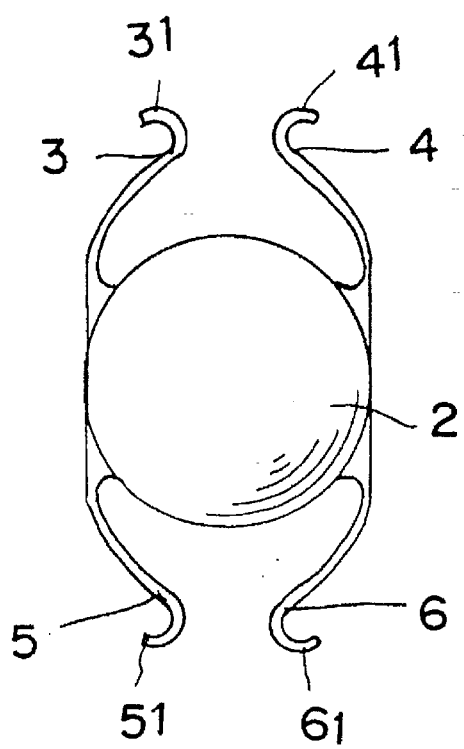
FIG. 1 is a front elevation of an intraocular lens taken as a preferred embodiment of the invention.

As best shown in FIG. 1, an intraocular lens 1 taken as a preferred embodiment of the invention generally comprises a disk-shaped lens body 2 behaving as the optical portion of the lens 1, and four support legs or extensions 3 to 6 extending from the lens body 2 to behave as support members.

The lens body 2 has a diameter of about 6 mm, which is as large as conventional anterior chamber lenses, and is made of polymethyl methacrylate or any other appropriate material so far approved for use as intraocular lenses.

The support legs 3 to 6 are made of polymethyl methacrylate or another stable material having an appropriate resiliency and hardness like those used for making support legs of conventional intraocular lenses to be placed in anterior chambers. Each of the support legs 3 to 6 is an elongated element having a diameter of about 0.2 mm, for example.

Figure 2:
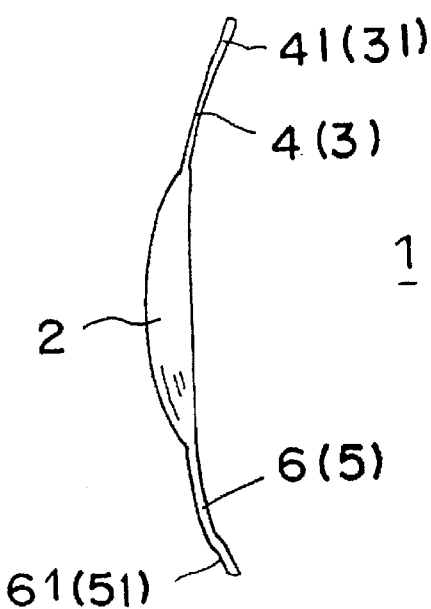
FIG. 2 is a side elevation of the same intraocular lens.

Two of the support legs, 3 and 4, are opposed face to face to each other and extend in a first direction, i.e. upwardly in FIGS. 1 and 2. The other support legs, 5 and 6, are also opposed face to face to each other but extend in a second direction opposite from the first direction, i.e. downwardly in FIGS. 1 and 2.

The support legs 3 to 6 moderately curve concavely, as best shown in FIG. 2, such that they can engage with ciliary sulci after penetrating a peripheral site 8 of an iris when the lens 1 is inserted in an anterior chamber 7. Moreover, distal ends of the support legs 3 to 6 are bent to form engaging portions 31, 41, 51 and 61.

Two of the support legs, 3 and 4, extending upwardly, make a first pair, while the other support legs 5 and 6, extending downwardly, make a second pair. As best shown in FIG. 1, the support legs in each pair curve inwardly to gradually diminish the relative distance between them. Then, their engaging portions, 31 and 41, 51 and 61, are bent back outwardly, to form an approximately semicircular arc.

When using the intraocular lens according to the embodiment, after surgery such as extracapsular cataract extraction and ultrasonic emulsifying aspiration, or after surgery such as intracapsular cataract extraction, fine through bores or apertures 10 as small as 0.5 to 1 mm, for example, are formed in a peripheral site of the iris 8 via the cornea 11 so that the support legs 3, 4, 5 and 6 can pass through the fine apertures 10.

Figure 3:
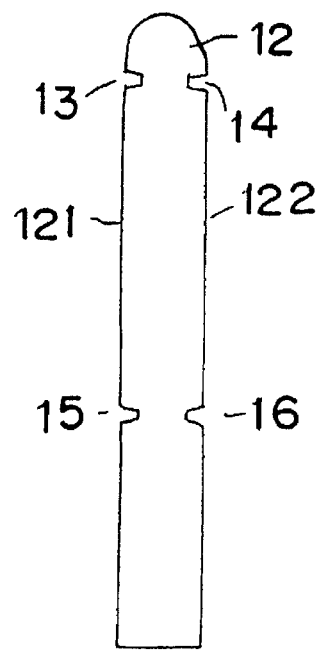
FIG. 3 is a plan view of a lens glide used for making through bores or apertures in a peripheral site of an iris.
Figure 4:
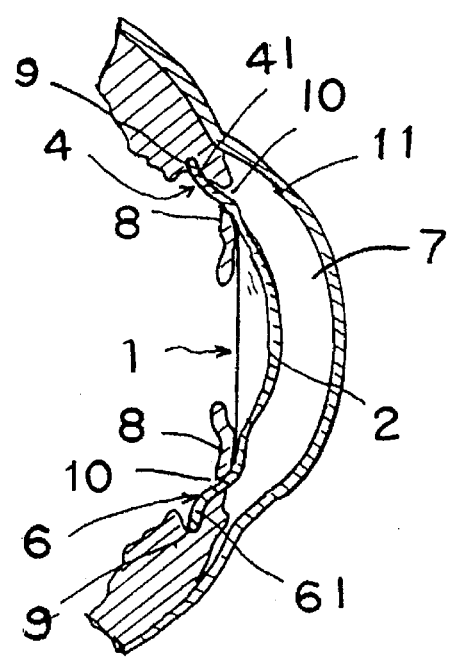
FIG. 4 is a diagram showing how the intraocular lens is fixed in place of an eye.

A lens glide plate 12 as shown in FIG. 3 will assist the operation for making the fine apertures 10 at precise positions.

The lens glide plate 12 is a plate-shaped member having guide grooves 13, 14, 15 and 16 along its opposite side edges 121 and 122. Relative distances and locations of the guide grooves 13 to 16 correspond to those of the support legs 3 to 6 of the intraocular lens 1.

The lens glide plate 12, when used, is placed on the cornea 11. Then a fine cutter is fit to the guide grooves 13 to 16 and pierced through the cornea 11 into the peripheral site of the iris 8. Thus the desired small apertures 10 are formed at proper positions of the iris 8 (not illustrated in detail).

The use of the lens glide plate 12 also serves to prevent vitreous creeps over the intraocular lens 1 when the lens 1 is inserted in the chamber.

After the foregoing preparation, while the lens body 2 is inserted in the anterior chamber 7, the support legs 3 to 6 are inserted into the respective apertures 10 in the iris 8 until the engaging portions 13 to 16 at their distal ends go beyond the iris 8 and engagingly sit in the ciliary sulci 9. Thus the intraocular lens 1 is reliably fixed in the anterior chamber 7.

As apparent from the explanation made so far, the intraocular lens 1 according to the embodiment can be inserted very easily, and is reliably fixed in position by engagement of its support legs 3 to 6 with the ciliary sulci through fine bores or apertures 10 in the peripheral site of the iris 8, which may be so small that they do not disturb the motion of the iris. Therefore, this intraocular lens 1 removes the possibility of any trouble in the corneal endothelium after surgery.

The use of four support legs 3 to 6 in the above-described embodiment is more advantageous for preventing a rotational motion of the intraocular lens 1 in the anterior chamber 7 and to remove the possibility of damaging the iris 8 and the cornea 11 after surgery. However, substantially the same effect is expected also when the total number of support legs is three, namely, one support leg extending in the first direction (upward) and two legs extending in the second direction (downward), or vice versa.

As described above, the intraocular lens according to the invention is an anterior chamber lens for implantation in the anterior chamber, which needs neither the high skill required for conventional posterior chamber lenses for placement in the posterior chamber to suture them to ciliary sulci, nor expensive apparatus for removal of vitreous which was also required for conventional posterior chamber lenses. Moreover, unlike conventional anterior chamber lenses, the intraocular lens according to the invention does not cause any trouble in the cornea, even after long use after surgery, because of its reliable fixture in the anterior chamber by reliable and unharmful engagement of its support legs with ciliary sulci.

No need of removal of vitreous not only ensures safe implantation of the intraocular lens but also contributes to reducing the time required for surgery.

Moreover, unlike conventional anterior chamber lenses fixed by engagement of its support legs with the anterior chamber angle, the intraocular lens according to the invention is held in position by engagement of its support legs with ciliary sulci through fine bores or apertures made in a peripheral site of the iris where the desired motion of the iris is not disturbed. Therefore, the intraocular lens is held in a remarkably stable condition, and removes the possibility of damages to the iris and the corneal endothelium caused by rotation or other motional displacement of the lens after surgery.

In particular, when using four support legs with two pairs of legs extending in opposite directions, the intraocular lens is more reliably fixed in position.

The intraocular lens according to the invention has a relatively simple structure, although having support legs extending from the lens body, which is not unreasonably complex as compared to conventional intraocular lenses for placement in the anterior chamber. Therefore, it can be fabricated easily while ensuring a sufficient durability.

Although the invention has been shown and described with respect to preferred embodiments thereof, it should be understood by those skilled in the art that the foregoing and other changes and omissions in the form and detail thereof may be made therein without departing from the spirit and scope of the invention, which is to be limited and defined only as set forth in the following claims.

What is claimed is:

1. An intraocular lens to be implanted in an anterior chamber, comprising:

a lens body having an anterior side and a posterior side; and elongated extensions extending from said lens body, which are long enough for their distal ends to engagingly sit in ciliary sulci and are curved concavely in a posterior direction with a curvature large enough for said lens body and part of said elongated extensions lying in the anterior chamber to be held offset from a plane of movement of an iris when said elongated extensions are inserted in and through fine apertures made in radially outer circumferential portions of the iris, each of said elongated extensions being bent radially outwardly at a distal end portion thereof and being bent rapidly inwardly immediately adjacent said distal end portion.

2. The intraocular lens according to claim 1, wherein the number of said elongated extensions are at least three, one or more of said elongated extensions extending in a first direction, and the other or others of said elongated extensions extending in a second direction opposite from said first direction.

* * * * *